(12) United States Patent
Mathiowetz et al.

(10) Patent No.: US 10,268,180 B2
(45) Date of Patent: Apr. 23, 2019

(54) HANDHELD FIELD MAINTENANCE TOOL WITH SIMULATION OF FIELD DEVICE FOR INSTRUCTION OR QUALIFICATION

(75) Inventors: Brad N. Mathiowetz, Lakeville, MN (US); Christopher P. Kantzes, Minneapolis, MN (US); Todd M. Toepke, Eden Prairie, MN (US); Kun Yang, Eden Prairie, MN (US); Adam E. Lund, St. Louis Park, MN (US)

(73) Assignee: FISHER-ROSEMOUNT SYSTEMS, INC., Austin, TX (US)

( * ) Notice: Subject to any disclaimer, the term of this patent is extended or adjusted under 35 U.S.C. 154(b) by 0 days.

(21) Appl. No.: 13/191,626

(22) Filed: Jul. 27, 2011

(65) Prior Publication Data
US 2012/0040316 A1 Feb. 16, 2012

Related U.S. Application Data

(60) Provisional application No. 61/368,477, filed on Jul. 28, 2010.

(51) Int. Cl.
*G05B 19/409* (2006.01)
*G06Q 20/20* (2012.01)
(Continued)

(52) U.S. Cl.
CPC ........ *G05B 19/409* (2013.01); *C07C 29/1518* (2013.01); *G05B 19/042* (2013.01);
(Continued)

(58) Field of Classification Search
CPC .... G09B 9/00; G05B 19/042; G05B 19/0426; G05B 19/4068; G05B 19/409;
(Continued)

(56) References Cited

U.S. PATENT DOCUMENTS 3,815,262 A * 6/1974 Patterson et al. ............... 434/35
4,425,097 A * 1/1984 Owens ..................... G09B 9/04
434/219

(Continued)

FOREIGN PATENT DOCUMENTS

CN 101763576 6/2010
DE 10245176 4/2004
(Continued)

OTHER PUBLICATIONS

US Statutory Invention Registration H1273—Apparatus and Method for Training a Technician to Diagnose internal Combustion Engine Malfuncitons—Novick, John—Jan. 1994.*
(Continued)

*Primary Examiner* — Timothy A Musselman
(74) *Attorney, Agent, or Firm* — Christopher R. Christenson; Kelly, Holt & Christenson PLLC

(57) ABSTRACT

A handheld field maintenance tool includes a training mode. The handheld field maintenance tool has a process communication module operably coupleable to a field device, a user interface, and a controller coupled to the process communication module and the user interface. The controller is configured to interact with a user through the user interface, and is configured to provide a simulation function where at least one characteristic of the field device, indicated through the user interface, is generated by the controller instead of the field device.

15 Claims, 8 Drawing Sheets

(51) Int. Cl.

| | | |
|---|---|---|
| *G06Q 40/04* | (2012.01) | |
| *C07C 29/151* | (2006.01) | |
| *G06Q 10/06* | (2012.01) | |
| *G06Q 30/06* | (2012.01) | |
| *G05B 19/042* | (2006.01) | |
| *G05B 19/4068* | (2006.01) | |

(52) U.S. Cl.
CPC ..... *G05B 19/0426* (2013.01); *G05B 19/4068* (2013.01); *G06Q 10/06315* (2013.01); *G06Q 20/204* (2013.01); *G06Q 30/0601* (2013.01); *G06Q 40/04* (2013.01); *G05B 2219/23018* (2013.01); *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01); *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01); *G05B 2219/50193* (2013.01); *Y02P 90/14* (2015.11); *Y04S 10/54* (2013.01)

(58) Field of Classification Search
CPC .......... G05B 2219/23018; G05B 2219/23054; G05B 2219/23126; G05B 2219/23163; G05B 2219/23406; G05B 2219/23445; G05B 2219/23446; G05B 2219/24001; G05B 2219/24056; G05B 2219/25062; G05B 2219/25428; G05B 2219/31121; G05B 2219/31197; G05B 2219/31475; G05B 2219/32007; G05B 2219/32144; G05B 2219/32226; G05B 2219/33331; G05B 2219/35422; G05B 2219/35429; G05B 2219/36122; G05B 2219/36128; G05B 2219/50193; G07C 29/1518; G06Q 20/204; G06Q 30/0601; G06Q 40/04; Y02P 90/14; Y04S 10/54
USPC ........................................................ 434/1–71
See application file for complete search history.

(56) References Cited

U.S. PATENT DOCUMENTS

| | | | |
|---|---|---|---|
| 4,613,952 A * | 9/1986 | McClanahan ................ 703/6 |
| 5,147,206 A * | 9/1992 | Golenski .................... 434/219 |
| 5,195,392 A | 3/1993 | Moore et al. ............. 73/866.5 |
| 5,273,434 A * | 12/1993 | Peck .................. G09B 19/0053 434/224 |
| 5,309,351 A | 5/1994 | McCain et al. ............. 364/132 |
| 5,442,632 A | 8/1995 | Crowder et al. ........... 371/20.1 |
| 5,903,455 A | 5/1999 | Sharpe, Jr. et al. ........ 364/188 |
| 6,033,226 A * | 3/2000 | Bullen ....................... 434/219 |
| 6,211,649 B1 | 4/2001 | Matsuda .................... 320/115 |
| 6,236,223 B1 | 5/2001 | Brady et al. ............. 324/750.3 |
| 6,377,859 B1 | 4/2002 | Brown et al. ................ 700/79 |
| 6,629,059 B2 | 9/2003 | Borgeson et al. .......... 702/183 |
| 6,633,782 B1 | 10/2003 | Schleiss et al. .............. 700/26 |
| 6,725,182 B2 | 4/2004 | Pagnano et al. ........... 702/188 |
| 6,971,063 B1 | 11/2005 | Rappaport et al. ......... 715/733 |
| 7,013,184 B2 | 3/2006 | Romagnoli et al. .......... 700/17 |
| 7,098,771 B2 | 8/2006 | Lefebvre et al. |
| 7,117,122 B2 | 10/2006 | Zielinski et al. ........... 702/183 |
| 7,120,391 B2 | 10/2006 | Stengele et al. ............ 455/41.3 |
| 7,188,200 B2 | 3/2007 | Griech ........................ 710/100 |
| 7,337,369 B2 | 2/2008 | Barthel et al. ................. 714/43 |
| 7,400,255 B2 | 7/2008 | Horch ..................... 340/572.7 |
| 7,421,531 B2 | 9/2008 | Rotvold et al. .............. 710/315 |
| 7,454,252 B2 | 11/2008 | El-Sayed ...................... 700/21 |
| 7,505,819 B2 | 3/2009 | El-Sayed ...................... 700/21 |
| 7,506,812 B2 | 3/2009 | von Mueller et al. ........ 235/449 |
| 7,675,406 B2 | 3/2010 | Baier et al. ................. 340/506 |
| 7,733,833 B2 | 6/2010 | Kalika et al. ............... 370/338 |
| 7,797,061 B2 | 9/2010 | El-Sayed ...................... 700/21 |
| 8,000,815 B2 | 8/2011 | John et al. ..................... 700/18 |
| 8,036,007 B2 | 10/2011 | Woehrle ........................ 363/65 |
| 8,059,101 B2 | 11/2011 | Westerman et al. .......... 345/173 |
| 8,060,862 B2 | 11/2011 | Eldridge et al. ............. 717/121 |
| 8,060,872 B2 | 11/2011 | Da Silva Neto ............. 717/177 |
| 8,074,172 B2 | 12/2011 | Kocienda et al. ............ 715/263 |
| 8,126,145 B1 | 2/2012 | Tewari et al. ................ 380/255 |
| 8,150,462 B2 | 3/2012 | Guenter et al. .............. 455/557 |
| 8,180,948 B2 | 5/2012 | Kreider et al. ............... 710/313 |
| 8,224,256 B2 | 7/2012 | Citrano, III et al. ....... 455/67.11 |
| 8,585,410 B2 | 11/2013 | Nielsen |
| 2001/0047504 A1 | 11/2001 | Aoyama ....................... 714/799 |
| 2002/0004370 A1 | 1/2002 | Stengele et al. ................ 455/39 |
| 2002/0007237 A1 | 1/2002 | Phung et al. ................... 701/33 |
| 2002/0027504 A1 | 3/2002 | Davis et al. ................. 340/540 |
| 2002/0086642 A1 | 7/2002 | Ou et al. ........................ 455/69 |
| 2002/0133322 A1 * | 9/2002 | Williams ........................ 703/8 |
| 2002/0171558 A1 | 11/2002 | Bartelheim et al. ..... 340/825.49 |
| 2003/0050737 A1 | 3/2003 | Osann, Jr. .................. 700/276 |
| 2003/0109937 A1 | 6/2003 | Zielinski et al. .................. 700/1 |
| 2003/0204373 A1 | 10/2003 | Zielinski et al. ............. 702/184 |
| 2003/0229472 A1 | 12/2003 | Kantzes et al. .............. 702/183 |
| 2004/0017221 A1 * | 1/2004 | Agarwal .......... H03K 19/17704 326/38 |
| 2004/0039458 A1 | 2/2004 | Mathiowetz et al. .......... 700/17 |
| 2004/0111238 A1 | 6/2004 | Kantzes et al. .............. 702/183 |
| 2004/0193287 A1 | 9/2004 | Lefebvre et al. ................ 700/1 |
| 2004/0204193 A1 | 10/2004 | Li et al. ..................... 455/575.1 |
| 2004/0228184 A1 | 11/2004 | Mathiowetz ................. 365/202 |
| 2004/0230327 A1 | 11/2004 | Opheim et al. ................ 700/83 |
| 2005/0138348 A1 * | 6/2005 | Bolay ................. G06F 9/44505 713/100 |
| 2005/0164684 A1 * | 7/2005 | Chen .................. G05B 19/0423 455/414.1 |
| 2005/0222698 A1 | 10/2005 | Eryurek et al. ................ 700/90 |
| 2005/0223120 A1 | 10/2005 | Scharold et al. ................ 710/1 |
| 2006/0014533 A1 | 1/2006 | Warren ......................... 455/423 |
| 2006/0087402 A1 | 4/2006 | Manning et al. .............. 340/3.1 |
| 2006/0161393 A1 | 7/2006 | Zielinski et al. |
| 2006/0206277 A1 | 9/2006 | Horch .......................... 702/82 |
| 2006/0290496 A1 | 12/2006 | Peeters ...................... 340/572.1 |
| 2006/0291438 A1 | 12/2006 | Karschnia et al. ........... 370/338 |
| 2007/0161352 A1 | 7/2007 | Dobrowski et al. .......... 455/69 |
| 2007/0161371 A1 | 7/2007 | Dobrowski et al. ......... 455/423 |
| 2007/0179645 A1 | 8/2007 | Nixon et al. .................. 700/83 |
| 2007/0208279 A1 | 9/2007 | Panella et al. ................ 600/595 |
| 2008/0114911 A1 | 5/2008 | Schumacher .................. 710/72 |
| 2008/0234837 A1 | 9/2008 | Samudrala et al. ............ 700/19 |
| 2008/0268784 A1 | 10/2008 | Kantzes et al. .............. 455/66.1 |
| 2009/0065578 A1 | 3/2009 | Peterson et al. ............. 235/382 |
| 2009/0094466 A1 | 4/2009 | Matthew et al. ............. 713/300 |
| 2009/0125713 A1 | 5/2009 | Karschnia et al. ........... 713/153 |
| 2009/0171483 A1 | 7/2009 | Scheuermann ................ 700/83 |
| 2009/0177970 A1 | 7/2009 | Jahl et al. .................... 715/735 |
| 2009/0181356 A1 * | 7/2009 | Dasgupta ................. G09B 7/00 434/362 |
| 2009/0271726 A1 | 10/2009 | Gavimath et al. ............ 715/771 |
| 2009/0284390 A1 | 11/2009 | Lahner et al. ........... 340/825.49 |
| 2009/0296601 A1 | 12/2009 | Citrano et al. .............. 370/254 |
| 2009/0326852 A1 | 12/2009 | Vetter et al. .................. 702/108 |
| 2010/0100766 A1 | 4/2010 | Bengtsson et al. ........... 714/23 |
| 2010/0114347 A1 | 5/2010 | Dheenathayalan et al. .... 700/97 |
| 2010/0114549 A1 | 5/2010 | Kolavi ........................ 703/13 |
| 2010/0145476 A1 | 6/2010 | Junk et al. ....................... 700/7 |
| 2010/0220630 A1 | 9/2010 | Kalika et al. ................ 370/254 |
| 2010/0290084 A1 | 11/2010 | Russell, III et al. ......... 358/1.15 |
| 2010/0290351 A1 | 11/2010 | Toepke et al. ............... 370/250 |
| 2010/0290359 A1 | 11/2010 | Dewey et al. ............... 370/252 |

(56) References Cited

U.S. PATENT DOCUMENTS

| | | | | |
|---|---|---|---|---|
| 2010/0293363 | A1 | 11/2010 | Meyer et al. | 713/1 |
| 2010/0330542 | A1* | 12/2010 | Nielsen | G09B 19/00 434/219 |
| 2011/0117529 | A1* | 5/2011 | Barash et al. | 434/265 |
| 2011/0238188 | A1 | 9/2011 | Washiro | 700/19 |
| 2012/0038458 | A1 | 2/2012 | Toepke et al. | 340/6.1 |
| 2012/0038548 | A1 | 2/2012 | Toepke et al. | 345/156 |
| 2012/0038760 | A1 | 2/2012 | Kantzes et al. | 348/61 |
| 2012/0040698 | A1 | 2/2012 | Ferguson et al. | 455/457 |
| 2012/0041744 | A1 | 2/2012 | Kantzes et al. | 703/13 |
| 2012/0046911 | A1 | 2/2012 | Mathiowetz et al. | 702/184 |

FOREIGN PATENT DOCUMENTS

| | | |
|---|---|---|
| DE | 102007035158 | 1/2009 |
| DE | 102008029406 | 12/2009 |
| DE | 102009028195 | 2/2011 |
| EP | 1515208 | 3/2005 |
| EP | 1916582 | 4/2008 |
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | 11296063 | 10/1999 |
| JP | 2001337004 | 7/2001 |
| JP | 2002062797 A | 2/2002 |
| JP | 2004060464 A | 2/2004 |
| JP | 2007-91381 | 4/2007 |
| JP | 2008165193 | 7/2008 |
| JP | 2008165193 A | 7/2008 |
| KR | 20060078883 | 7/2006 |
| RU | 2007121658 | 12/2008 |
| WO | WO 01/35190 | 5/2001 |
| WO | WO 02/086662 | 10/2002 |
| WO | WO 2006/016845 | 2/2006 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO 2009/074544 | 6/2009 |

OTHER PUBLICATIONS

Invitation to Pay Additional Fees for international patent application No. PCT/US2010/034889 dated Sep. 15, 2010.
ABB Limited: "Wireless Instrumentation Jargon Buster". Information bulletin instrumentation ABB No. IB/INST-018, Mar. 3, 2009, XP002596601. Retrieved from the Internet: URL:http://www05.abb.com/global/scot/scot203.nsf/veritydisplay/be00ec76ef07e978c125756e003157b9/$File/IB_INST_018_1.pdf.
Notification of Transmittal of the International Search Report and the Written Opinion from the International Application No. PCT/US2010/021764.
David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT%202009:003.pdf.
Notification of Transmittal of the International Search Report and the Written Opinion for the International application No. PCT/US2010/034848 dated Aug. 26, 2010.
Possio Bluetooth to WLAN Gateway PX20: Full Product Description retrieved from http://www.blueunplugged.com/p.aspx?p=105816.
1420 Wireless Gateway: Product Data Sheet 00813-0100-4420, Rev BA Mar. 2008. Emerson Process Management.
Smart Wireless Gateway (WirelessHART™). Quick Installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(1) and 162 EPC for European patent application No. 10701430.0 dated Aug. 30, 2011.
Invitation to Pay Additional Fees for international patent application No. PCT/US2010/034949 dated Sep. 17, 2010.
Technical Data Sheet: VIATOR® USB HART® Interface (Model 010031). MACTek Measurement and Control Technologies.
VIATOR® Bluetooth® Wireless Technology Interface for use with HART field devices. MACTek Measurement and Control Technologies retrieved from www.mactekcorp.com/product5.htm.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
First Communication from related European patent application No. 107255432 dated Oct. 11, 2012.
First Communication from related European patent application No. 107302796 dated Oct. 19, 2012.
Office Action from related Russian application No. 2011151063 dated Nov. 12, 2012.
First Office Action from related Japanese application No. 2015511048, dated Jan. 29, 2013.
1420 Wireless Gateway. Reference Manual 00809-0100-4420, Rev BA. Aug. 2007. Emerson Process Management.
Invitation to pay additional fees from the related International patent application No. PCT/US2011/045679 dated Aug. 6, 2012.
Invitation to pay additional fees from the related International patent application No. PCT/US2011/045664 dated Aug. 9, 2012.
Invitation to pay additional fees from the related International patent application No. PCT/US2011/045676 dated Jul. 30, 2012.
Lee S W et al: "Honam Petrochemical Corporation Uses Simulator for Ethylene Plant Operator Training", Processing of the Industrial Computing Conference. Houston, Oct. 18-23, 1992. pp. 219-222.
Kurrle H-P et al.: "Trainingssimulator Zur Ausbildung Von Chemikanten und Anlagenfahrern. Otraining Simulator for the Training of Process Workers (Chemikanten) and Operators", Automatisierungstechnische Praxis—ATP, Oldenbourg Indusrieverlag, Munchen, DE, vol. 36, No. 7, Jul. 1, 1994. Abstract, Section 2.
International Search Report and the Written Opinion of the International Searching Authority for International patent application No. PCT/US2011/045676 filed Jul. 28, 2011.
First Office Action from counterpart Japanese patent application No. 2013-521966, dated Dec. 24, 2013. 7 pages.
Office Action from Japanese patent application No. 2013-521968, dated Jan. 21, 2014, 7 pages.

(56) References Cited

OTHER PUBLICATIONS

First Office Action from Chinese patent application No. 201180001611. 2, dated Apr. 3, 2014. 14 pages.
Office Action from Counterpart Russian Patent Application No. 2013108780 dated Oct. 24, 2014, 10 pages.
Office Action from Canadian patent application No. 2,806,722, dated Jul. 28, 2014. 3 pages.
Office Action from Canadian patent application No. 2,806,564, dated Jul. 31, 2014. 5 pages.
Second Office Action from Chinese Patent Application No. 201180001611.2 dated Nov. 18, 2014, 9 pages with English Translation.
First Office Action for counterpart Chinese Patent Application No. 201180001617.X, dated Feb. 4, 2015, 15 pages.
Authors Unknown, Foundation Fieldbus Blocks, Fisher-Rosemout, 00809-0100-4783, Rev. BA, 2000, 102 pages.
Third Chinese Office Action for Chinese Patent Application No. 201180001617.X dated Mar. 10, 2016, 8 pages.
Second Chinese Office Action for Application No. 201180001617. X, dated Sep. 21, 2015, 8 pages.
Office Action for Canadian Patent Application No. 2,806,564 dated Jan. 11, 2016, 4 pages.
EPO Communication pursuant to Article 94(3) EPC for European Patent Application No. 11743721, dated Jun. 30, 2017, 8 pages.
Invitation to pay additional fees from the related International patent application No. PCT/US2011/045665 dated Aug. 23, 2012.
Bushman J B: "Ally: An Operator's Associate for Cooperative Supervisory Control Systems", IEEE Transactions on Systems, Man and Cybernetics, IEEE Inc. New York, US, vol. 23, No. 1, Jan. 1, 1993, pp. 111-128.
First Communication for the related European patent application No. 107302812 dated Oct. 11, 2012.
International Search Report and Written Opinion from the related International patent application No. PCT/US2011/045664 dated Nov. 6, 2012.
International Search Report and Written Opinion from the related International patent application No. PCT/US2011/045679 dated Nov. 6, 2012.
International Search Report and Written Opinion from the related International patent application No. PCT/US2011/045665 dated Nov. 6, 2012.
First Examination Report, dated Nov. 26, 2018, for Indian Patent Application No. 288/CHENP/2013, 8 pages.

* cited by examiner

HANDHELD FIELD MAINTENANCE TOOL WITH SIMULATION OF FIELD DEVICE FOR INSTRUCTION OR QUALIFICATION

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

A handheld field maintenance tool includes a training mode. The handheld field maintenance tool has a process communication module operably coupleable to a field device, a user interface, and a controller coupled to the process communication module and the user interface. The controller is configured to interact with a user through the user interface, and is configured to provide a simulation function where at least one characteristic of the field device, indicated through the user interface, is generated by the controller instead of the field device.

DETAILED DESCRIPTION

Figure 1A:
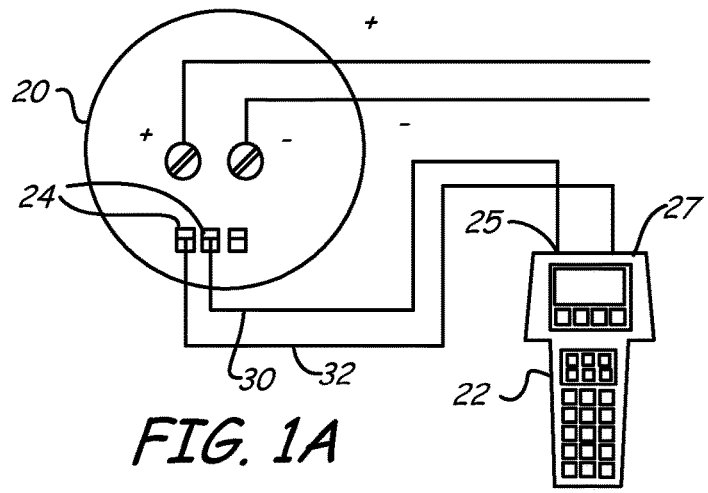
FIGS. 1A and 1B are diagrammatic views of a handheld field maintenance tool with which embodiments of the invention are particularly useful.
Figure 1B:
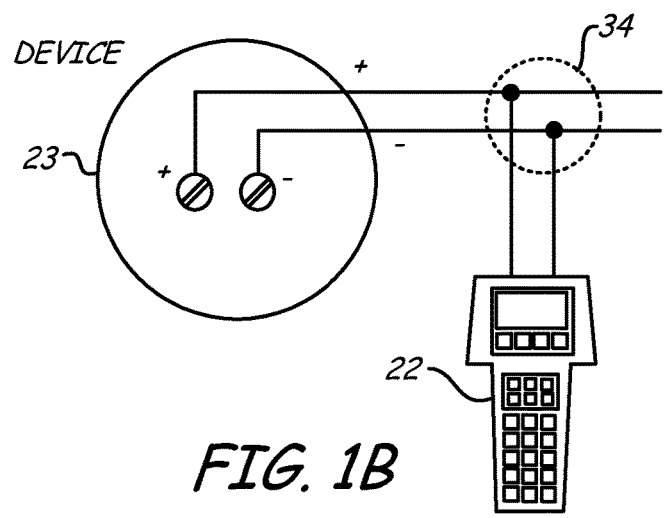

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
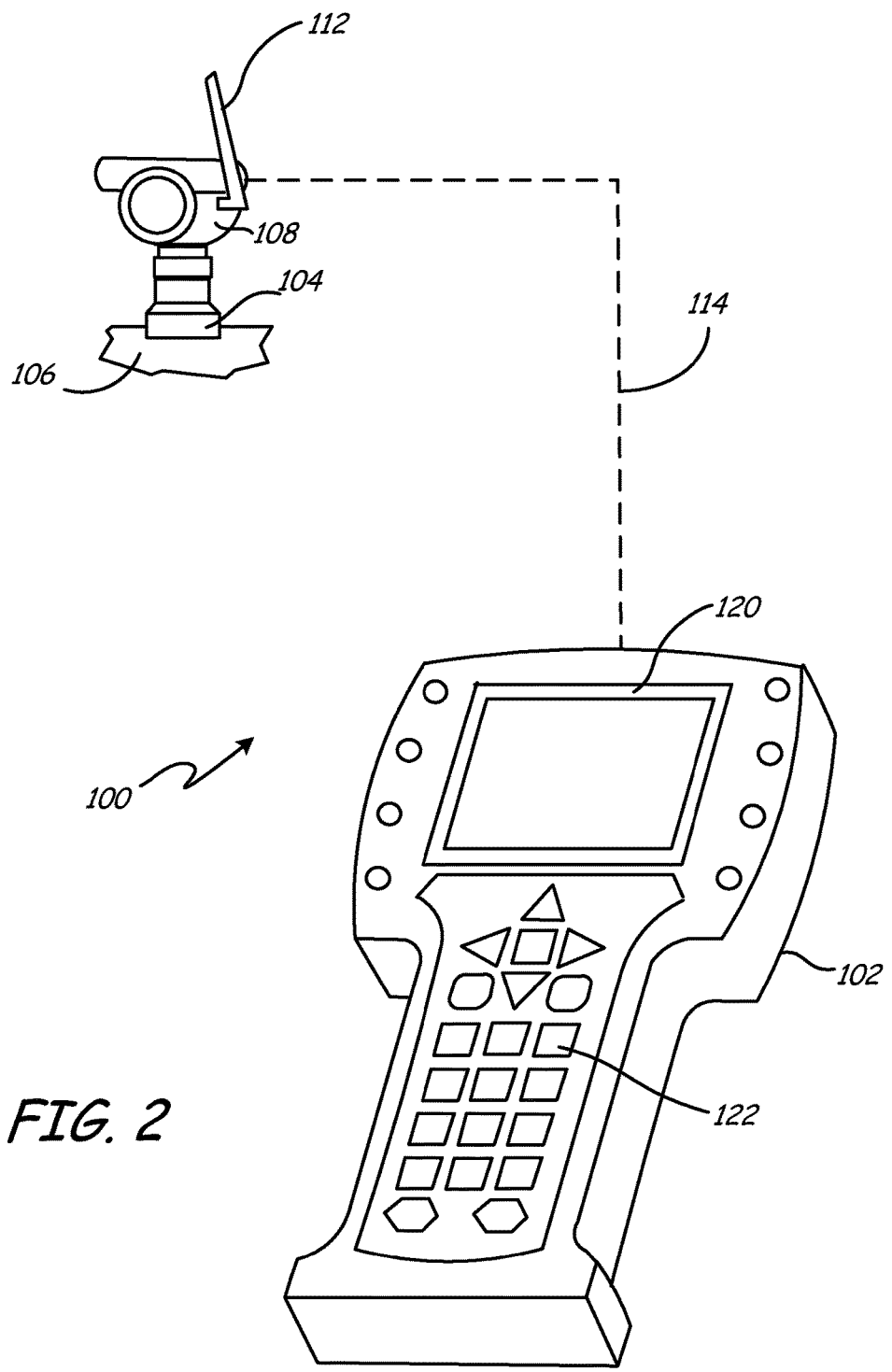
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus, Profibus and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
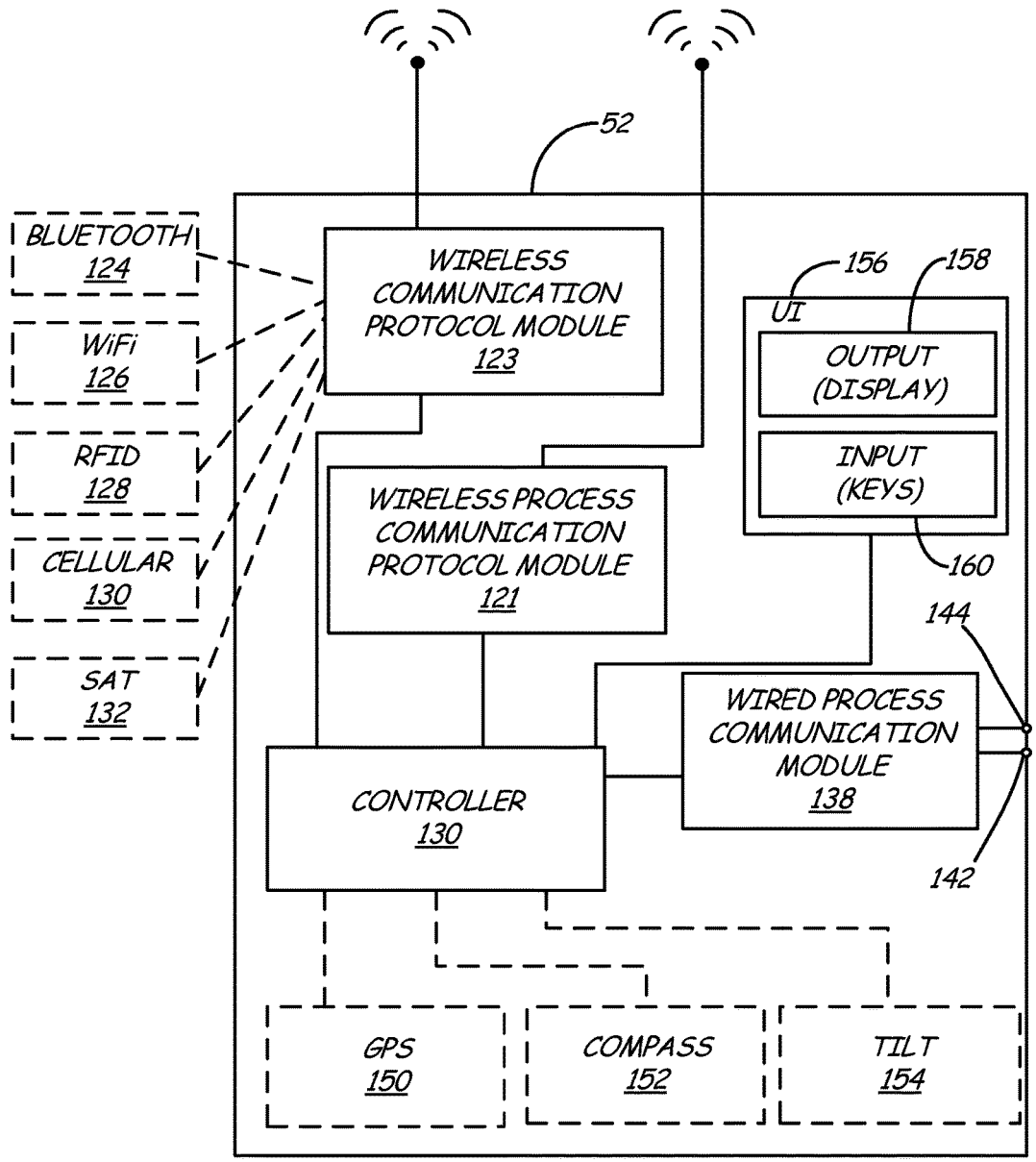
FIG. 3 is a block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 comply with at least one intrinsic safety specification, such as that listed above, in order to help ensure safety in potentially explosive environments. Handheld field maintenance tool 52 includes at least one wireless process communication module 121. Suitable examples for wireless process communication module 121 include a module that generates and/or receives proper signals in accordance with a known wireless communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2; a Wi-Fi specification 126 (such as IEEE 802.11.a/b/g/n); a known RFID specification 128; cellular communication techniques 130 (such as GSM/CDMA); and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138. Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the highway addressable remote transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further still, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

The positional location module 150, compass module 152 and tilt module 154 are particularly useful where a handheld field maintenance tool helps a technician or engineer find the physical location of a wireless field device in the field. An oil refinery is often a very large process installation with many field devices positioned at various locations, some of which may not be readily visible.

Proper field maintenance requires a well-trained technician. Such training is very rigorous in that technicians may be exposed to myriad field devices and various types of conditions and scenarios relative to each such field device. Not only must a technician be able to effectively install, calibrate, and/or commission a field device, in the event that the field device requires maintenance, the technician must quickly determine what type of maintenance is required, and perform such maintenance expeditiously. Accordingly, technician training is an extremely important aspect of proper field maintenance. Training a technician to configure and troubleshoot process field devices typically requires significant classroom instruction and lab time where students work directly with process field devices. While this environment is an essential part of the students' learning, since the field devices that the students train with are usually in very good working order, the students do not get much exposure to hands-on troubleshooting of field devices. More often than not, the students learn about troubleshooting in the classroom and may not actually be exposed to a "problem" field device until they are faced with an actual failure in an operating process installation. Even if a "problem" field device were available for the students to troubleshoot, the failure types would typically be extremely limited. For example, a disconnected sensor.

Embodiments of the present invention generally provide a handheld field maintenance tool with an ability to simulate field device interaction to facilitate instruction and/or qualification. In accordance with an embodiment of the present invention, controller 130 includes, or otherwise stores, a number of program instructions which when executed, provide the functions of a software application that generates a simulation mode on the handheld field maintenance tool. When the handheld field maintenance tool is running in simulation mode, its display is preferably identical to what a technician would see if the technician had connected to an actual device. To further enhance the experience, embodiments of the present invention even allow the student the ability to connect the handheld field maintenance tool to an actual device. In such embodiments, the transition from live device to simulation is preferably made with no indication to the user. Accordingly, the user or student believes that he or she is interacting with the actual physical field device when, in fact, the student is engaged in a simulation. In accordance with another embodiment of the present invention, a simulation module is provided that is physically coupled to the process wiring connections of a handheld field maintenance tool. Preferably, the physical module also includes additional process wired connections such that a user or student can still make physical connections to an actual device. However, the simulation module is interposed between the handheld field maintenance tool and the actual field device can generate simulated responses for the purposes of instruction and/or qualification, as will be described in greater detail below.

Figure 4:
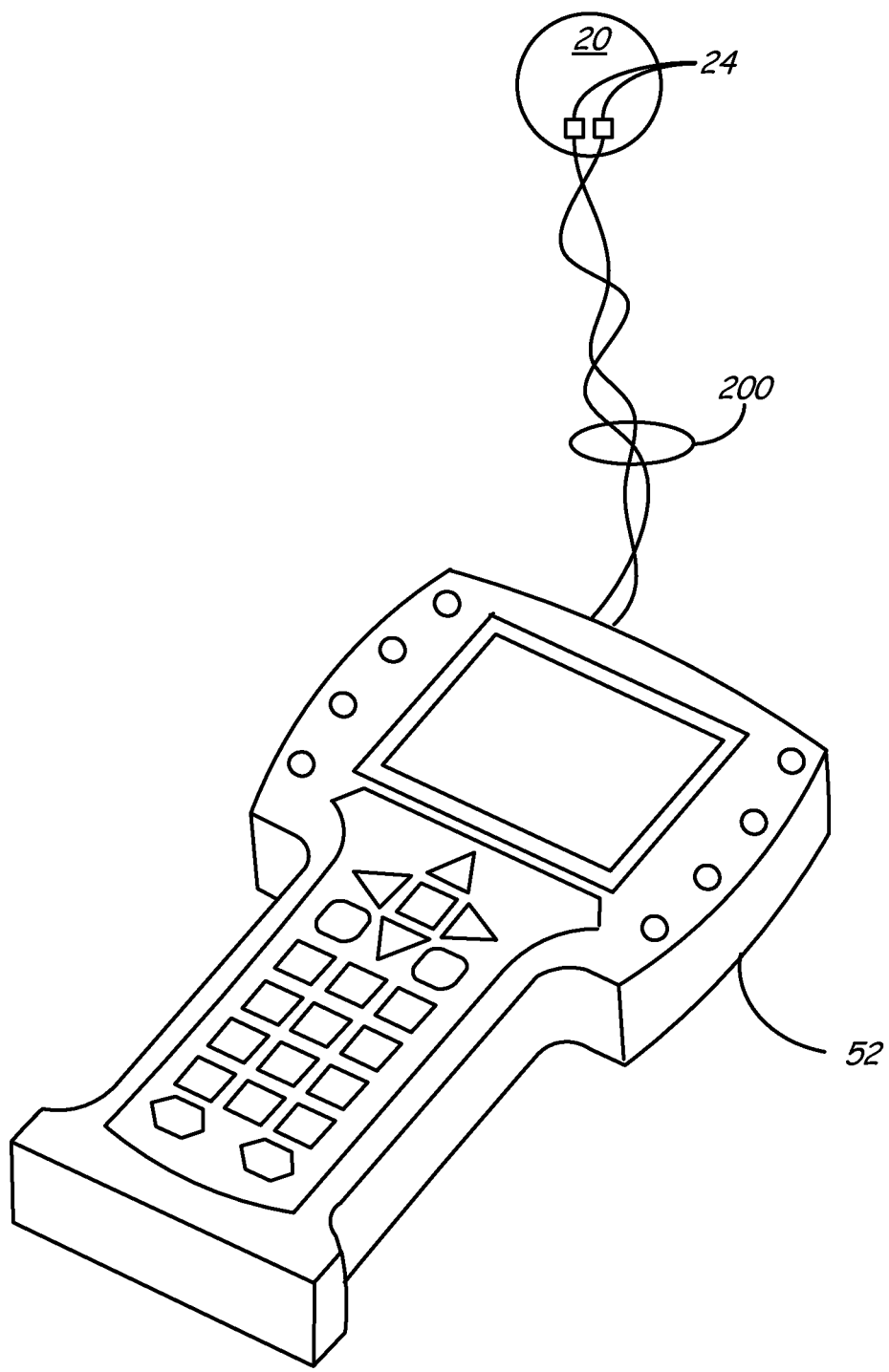
FIG. 4 is a diagrammatic view of a handheld field maintenance tool coupled to a field device for training purposes in accordance with an embodiment of the present invention.

FIG. 4 is a diagrammatic view of a handheld field maintenance tool coupled to a field device for training purposes. Handheld field maintenance tool 52 is illustrated being coupled via a wired connection 200 to terminals 24 of field device 20. When the simulation mode of handheld field maintenance tool 52 is invoked, or otherwise entered, controller 130 within handheld field maintenance tool 52 renders the user interface to the student in such a way that the student believes that he or she is actually interacting with field device 20. While this is preferably the case, embodiments of the present invention may also provide a user interface with a heading that indicates that the user is in a training mode. Regardless, in simulation mode, the software instructions stored within controller 130, or suitable memory coupled to controller 130, cause handheld field maintenance tool 52 to interact with the student in much the same way that a live handheld field maintenance tool would interact with a technician in the field. Moreover, handheld field maintenance tool 52 can include instructions stored therein that when executed cause the simulation mode to execute one or more maintenance scenarios. For example, a maintenance scenario might be the indication of an error or problem with respect to a field device. The technician would then be required to investigate the field device (simulated field device) using the handheld field maintenance tool to diagnose and potentially correct the problem. Preferably, the keystrokes and other interactions of the student during the simulation are logged such that they can be reviewed later in order to grade, or otherwise assess, the student's performance. During simulation mode, handheld field maintenance tool 52 may indicate on display 120, some actual live communication with field device 20. However, during the simulation, at least some of the responses indicated to the student via display 120 are not based upon actual interaction with field device 20. Instead, such responses are part of one or more scenarios being executed during the simulation.

Figure 5:
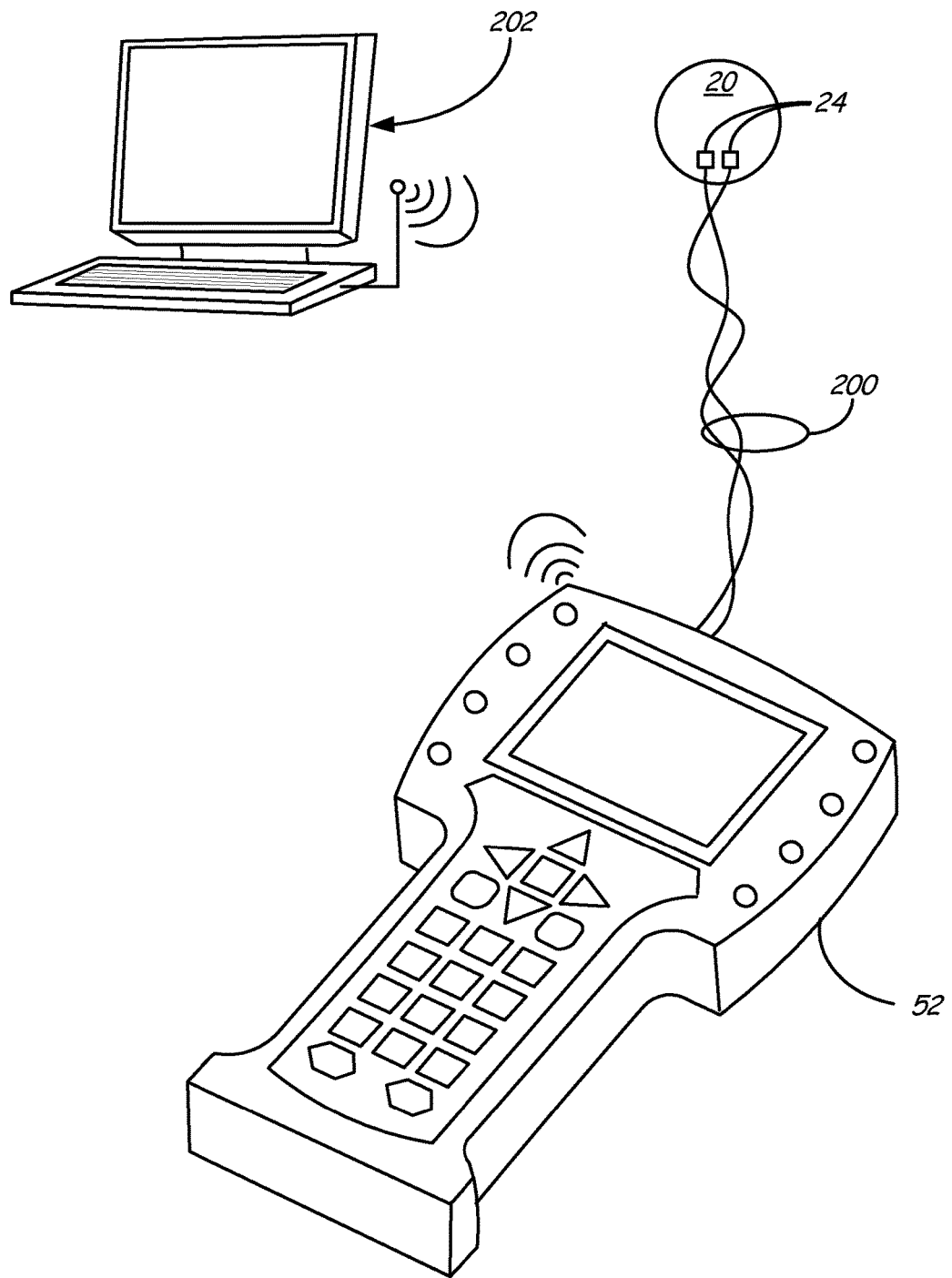
FIG. 5 is a diagrammatic view of a handheld field maintenance tool executing a field device training simulation in accordance with another embodiment of the present invention.

FIG. 5 is a diagrammatic view of a handheld field maintenance tool executing a device simulation in accordance with another embodiment of the present invention. FIG. 5 bears many similarities to FIG. 4, and like components are numbered similarly. The primary distinction between the embodiments illustrated in FIGS. 4 and 5, is the utilization of wireless communication between handheld field maintenance tool 52, and training workstation 202. As described above, with respect to FIG. 3, handheld field maintenance tool 52 preferably includes wireless communication protocol module 123. This allows handheld field maintenance tool 52 to communicate with training workstation 202 using any suitable wireless communication protocol. The utilization of wireless communication between handheld field maintenance tool 52 and training workstation 202 allows the simulation to be viewed by a trainer, stationed at workstation 202, in real-time. Moreover, as the trainer observes the simulation, the trainer also has the ability to modify the simulation during the course of the simulation, and/or in response to certain activities or actions performed by the student. In some remote embodiments, the trainer would only be able to review the steps the student pursued only after a given training scenario was completed.

Figure 6:
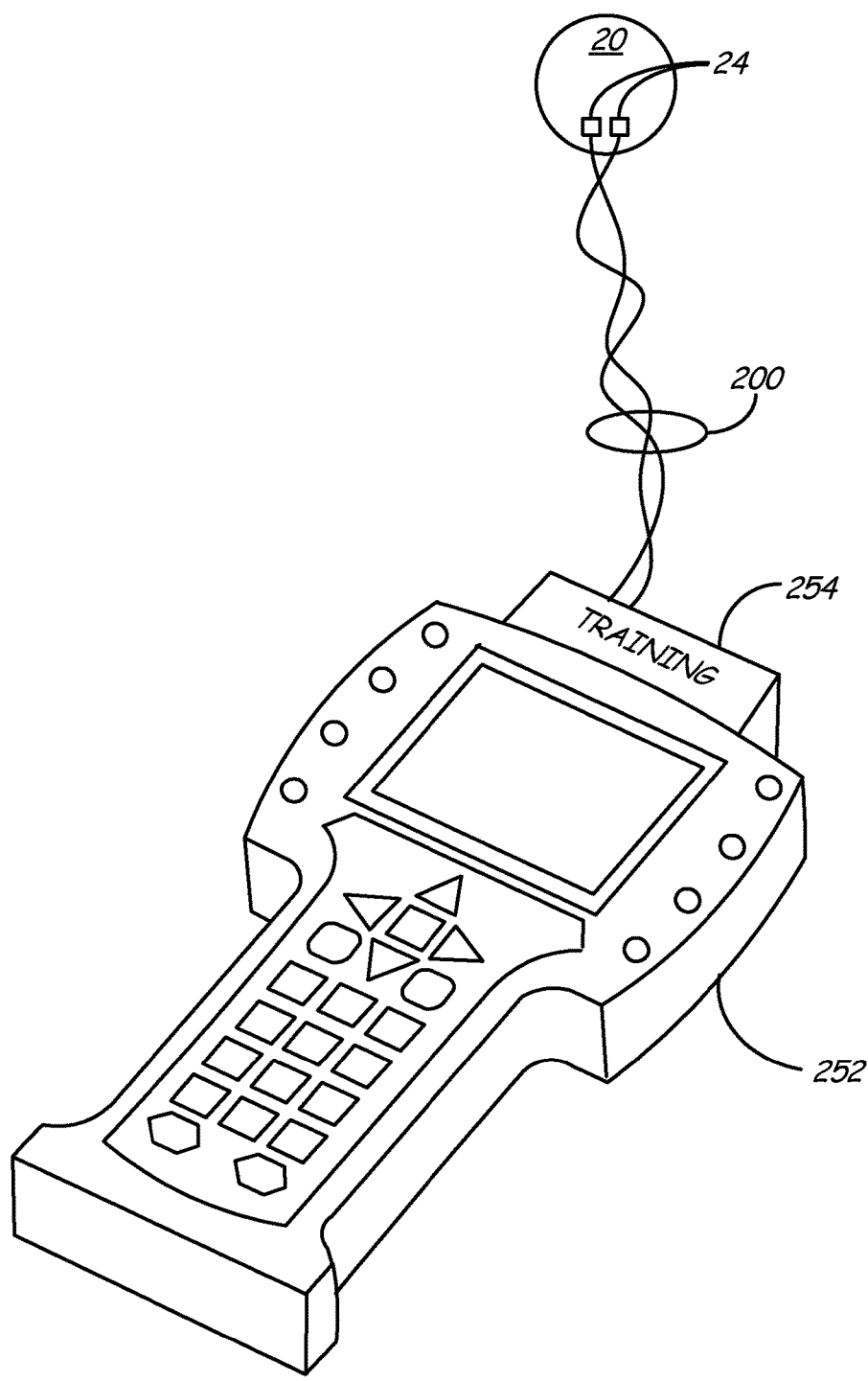
FIG. 6 is a diagrammatic view of a handheld field maintenance tool executing a field device training simulation in accordance with an embodiment of the present invention.

FIG. 6 is a diagrammatic view of a handheld field maintenance tool executing a training simulation in accordance with an embodiment of the present invention. FIG. 6 bears some similarities to FIG. 5, and like components are numbered similarly. In contrast to the embodiment illustrated in FIG. 5, FIG. 6 shows handheld field maintenance tool 252 coupled to external training module 254 through which the wired connection 200 to field device 20 is effected. Preferably, training module 254 is both electrically connected to the process wiring terminals of handheld field maintenance tool 252, and is also mechanically supported by such coupling as well. Examples of suitable electrical interconnections include the utilization of well-known banana plugs. Training module 254 is thus electrically interposed between handheld field maintenance tool 252 and field device 20. While handheld field maintenance tool 252 may be the same as handheld field maintenance tool 52, described above, it may also be a legacy handheld field maintenance tool that does not include device simulation capabilities. An example of such a tool is the Model 275 HART Communicator. In the embodiment illustrated in FIG. 6, the training function is wholly embodied within module 254. Module 254 is able to selectively allow communication with field device 20, and may also selectively disconnect from field device 20 (with or without the knowledge of the student) to perform a training simulation. Preferably, all digital communication from handheld field maintenance tool 252 is stored for evaluation by a trainer. While the embodiment illustrated in FIG. 6 may not be as optimal as the embodiments illustrated in FIGS. 4 and 5, where all individual key presses entered into the handheld field maintenance tool 52 are captured for later evaluation, the embodiment illustrated in FIG. 6 is useful in that the output of handheld field maintenance tool 252 can be captured for evaluation. Moreover, an important feature of the embodiment illustrated in FIG. 6 is that it can be used with handheld field maintenance tools or other communicators and field maintenance tools for which training simulation is not available as a native application or software solution.

Figure 7:
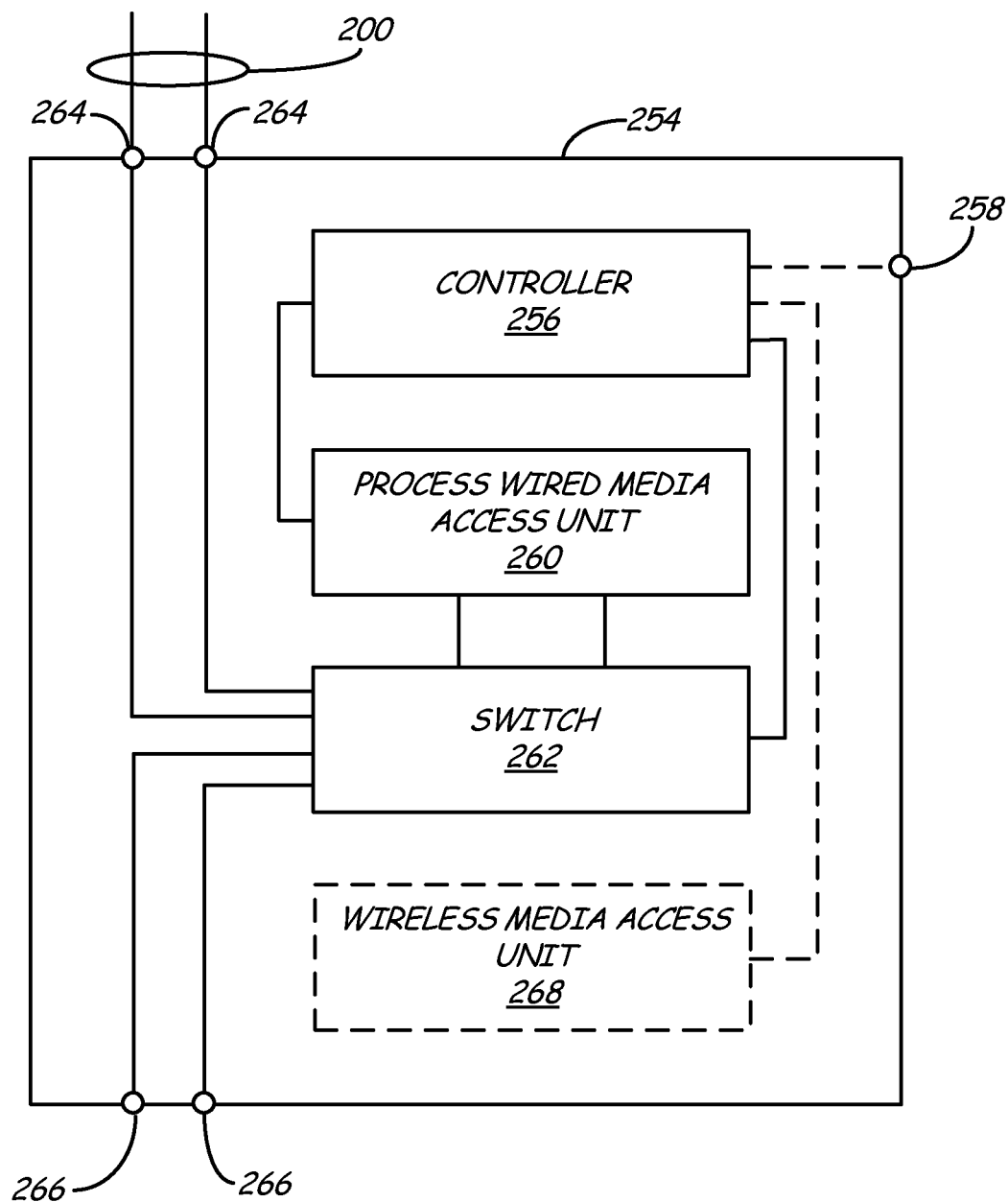
FIG. 7 is a block diagram of a training module in accordance with an embodiment of the present invention.

FIG. 7 is a block diagram of training module 254 in accordance with the embodiment of the present invention. Training module 254 includes its own controller 256 which is preferably coupled to a programming port 258, such as a USB port. Training module 254 also includes a process wired media access unit 260 coupled to controller 256. An example of a process wired media access unit is a HART® protocol media access unit, a Profibus media access unit, or a FOUNDATION™ Fieldbus media access unit. The process wired media access unit 260 is coupled by virtue of one or more connections to switch module 262 which is also coupled to controller 256. Switch module 262 is electrically interposed between output terminals 264 and input terminals 266. Accordingly, under control of controller 256, switch 262 can selectively allow training module 254 to electrically interpose itself in place of process wired connection 200, as appropriate. Preferably, controller 256 is programmed, or otherwise loaded with one or more training scenarios relative to one or more simulated field devices. Preferably, such programming is done via USB port 258, however any suitable communication with controller 256 may be used. For example, in some embodiments, a wireless media access unit 268 is coupled to controller 256 such that wireless communication, such as WiFi, Bluetooth, et cetera, can be used to communicate with controller 256. Additionally, in embodiments where wireless media access unit 268 is provided, an external device, such as training workstation 202 can communicate directly with controller 256 to monitor and/or modify a training scenario or student experience.

Figure 8:
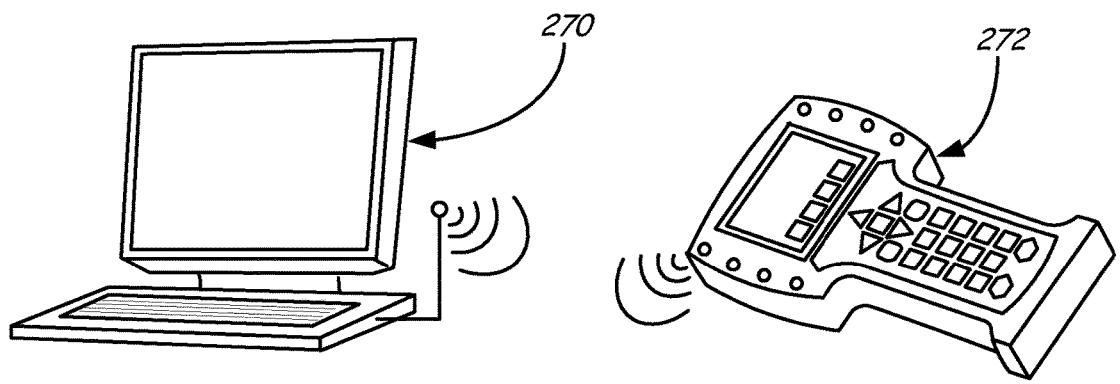
FIG. 8 is a diagrammatic view of a handheld field maintenance tool operating in a training or qualification simulation in accordance with an embodiment of the present invention.
Figure 8:
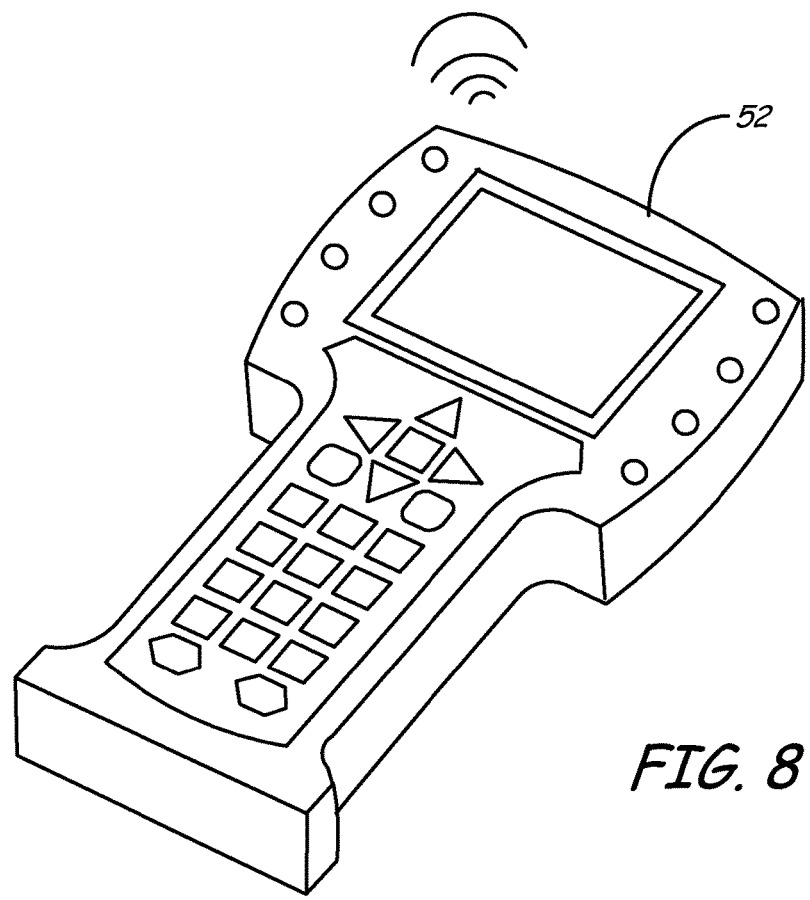

FIG. 8 is a diagrammatic view of a handheld field maintenance tool engaging in a training or qualification simulation in accordance with the embodiment of the present invention. Handheld field maintenance tool 52 by virtue of its wireless process communication protocol module 121 (shown in FIG. 3) is able to communicate with wireless field devices, such as WirelessHART field devices. In the embodiment illustrated in FIG. 8, the wireless communication between either training workstation 270, or training handheld 272 is in accordance with a wireless process communication protocol, such as WirelessHART. Thus, the student using handheld field maintenance tool 52 may believe that she or she is actually interacting with a wireless field device, when in fact, the actual interaction is with training workstation 270, or training handheld 272. Additionally, or alternatively, at least some of the training scenarios, or interactions provided to the user via handheld field maintenance tool 52 may employ a local training simulation application or software instructions resident within handheld field maintenance tool 52.

While many embodiments of the present invention have generally been described with respect to a field device coupled, either physically, or via wireless communication, to a handheld field maintenance tool for training purposes, embodiments of the present invention do not actually require such coupling. Instead, a training application resident upon, and executing within, a handheld field maintenance tool may simply emulate one or more field devices for training purposes. Further, in embodiments where a training module is physically coupled to a handheld field maintenance tool, the training module itself can, in some embodiments, provide all requisite interaction with the handheld field maintenance tool, such that physical coupling to an actual field device is not required.

One particular advantage of embodiments of the present invention that employ wireless communication, is that a trainer employing training workstation 202, 270, or handheld 272, can interact with more than one student at one time. In this manner, a trainer would have the ability to prompt the same scenario onto multiple handheld field maintenance tools or different scenarios on each, for situations where there is more than one student. This is particularly advantageous in large training classes.

Although the present invention has been described with reference to particular embodiments, workers skilled in the art will recognize that changes may be made in form and detail without departing from the spirit and scope of the invention.

What is claimed is:

1. A training module for a handheld field maintenance tool, the training module comprising:
   a first pair of terminals coupleable to a corresponding pair of terminals of a handheld field maintenance tool;
   a second pair of terminals coupleable to a field device of the type which measures and/or controls an industrial process;
   a process communication media access unit;
   a switch having a first mode, wherein the first and second pair of terminals are coupled together, and a second mode where the first pair of terminals is coupled to the process communication media access unit; and
   a controller physically coupled to the switch and the process communication media access unit, the controller being configured to control the switch to selectively simulate the field device, wherein selectively simulating the field device comprises presenting a user of the field device with at least one characteristic generated by the controller and at least one characteristic generated by the field device and communicated through the second pair of terminals when coupled to the field device, wherein the field device-generated characteristic and the controller-generated characteristic are presented to the user such that the user is unaware of which of the at least one characteristics is a simulated characteristic generated by the handheld field maintenance tool.

2. The training module of claim 1, and further comprising a wireless media access unit coupled to the controller to allow the controller to communicate with a remote wireless device.

3. The training module of claim 2, wherein selectively simulating the field device comprises:
   generating, by the controller, an indication of at least one of the controller-generated characteristic and the field device-generated characteristic; and
   providing, by the wireless media access unit, the indication to the remote wireless device.

4. The training module of claim 1, and further comprising a programming port coupled to the controller.

5. The training module of claim 4, wherein the programming port is a Universal Serial Bus (USB) port.

6. The training module of claim 1, wherein the switch is electrically interposed between the first pair of terminals and the second pair of terminals.

7. The training module of claim 1, wherein the switch is selectively interposed at a communication connection between the field device and the handheld field maintenance tool.

8. The training module of claim 1, wherein the controller stores instructions that, when executed, selectively simulate the field device.

9. The training module of claim 1, wherein the controller is configured to control the switch to enable communication, between the field device and the handheld field maintenance tool, upon entering the first mode.

10. The training module of claim 1, wherein the controller is configured to control the switch to enable communication, between the process communication media access unit and the handheld field maintenance tool, upon entering the second mode.

11. The training module of claim 10, wherein enabling communication comprises enabling communication between the process communication media access unit of the training module and a process communication module of the handheld field maintenance tool.

12. The training module of claim 1, wherein the training module comprises an electrical interconnection configured to physically couple the training module to the handheld field maintenance tool.

13. The training module of claim 1, wherein the process communication media access unit is coupled to the switch.

14. The training module of claim 1, wherein the controller is configured to identify an output of the handheld field maintenance tool.

15. The training module of claim 14, wherein the controller is configured to store training information, based on the output of the handheld field maintenance tool.

* * * * *